United States Patent [19]
Hudson et al.

[11] Patent Number: 5,801,004
[45] Date of Patent: Sep. 1, 1998

[54] METHOD FOR DETECTING PROSTATIC CANCER

[76] Inventors: Perry B. Hudson, 11598 Shelly Cir., Seminole, Fla. 33772; Michael E. Lombardo, 11579 Shelly Cir., Seminole, Fla. 33772-6145; Said I. Hakky, 8547 Merrimoor Blvd., E., Largo, Fla. 33777-3145

[21] Appl. No.: 771,963

[22] Filed: Dec. 23, 1996

[51] Int. Cl.$^6$ .................................................. G01N 33/53

[52] U.S. Cl. .................. 435/7.23; 530/387.7; 530/387.9

[58] Field of Search ........................ 435/7.1, 7.23; 530/387.7, 387.9

[56] References Cited

PUBLICATIONS

Silver, RI et al. 1994. J. Urology 152: 433–437.
Thigpen, A E et al. 1993. J. Clin. Invest. 92: 903–10.
Moreno, JG. et al. 1992. Cancer Res. 52:6110–12.
Morminoflan, R. et al. 1992. JBC. 267:19548–19554.

Primary Examiner—Sheela Huff
Assistant Examiner—Julie E. Reeves
Attorney, Agent, or Firm—John Lezdey and Associates

[57] ABSTRACT

A method for detecting prostatic cancer in patients by detecting the pressure of 5α-reductase type 2 isozyme in the serum or urine of the patients. The method preferably utilized a biomarker which is the polyclonal antibodies of a peptide representing amino acids 28 to 43 of the 5α-reductase type 2 isozyme.

3 Claims, No Drawings

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: Yes ( i v ) ANTI-SENSE: No ( v i ) ORIGINAL SOURCE: Serum ( x ) PUBLICATION INFORMATION:
        ( A ) AUTHORS: Thigpen, AC
            Silver, RI
            Guileyardo, JM
            Casey, MI
            McConnell, JD
            Russell, DW
        ( B ) TITLE: Tissue distribution and ontogeny of steriod 5d- reductase isozyme expression.

-continued (C) JOURNAL: J. Clin. Invest.
(D) VOLUME: 92
(F) PAGES: 903-910
(G) DATE: 1993
(K) RELEVANT RESIDUES IN SEQ ID NO: 1:

(i) SEQUENCE DESCRIPTION: SEQ ID NO:1:

Cys Ala Lys Pro Ser Gly Tyr Gly Lys His Thr Glu Ser Leu
1               5                       10

Lys Pro Ala
15

METHOD FOR DETECTING PROSTATIC CANCER

FIELD OF THE INVENTION

The present invention provides a method for detecting prostatic cancer and to novel peptides for use therein. More particularly, prostatic cancer is diagnosed in urine and serum through the use of polyclonal antibodies prepared to a peptide representing amino acids 28 to 43 of 5α-reductase type 2 isozyme.

BACKGROUND OF THE INVENTION

With the increase in life expectancy throughout the world has come an increasing incidence of prostate cancer. An estimated 200,000 men develop prostate cancer every year in the United States and approximately 38,000 will die of this disease every year. Metastatic disease will have already taken hold in the majority of the patients newly diagnosed with prostate cancer (2). The ideal biomarker would be found in the peripheral circulation, a premise not beyond the realm of possibilities if one considers the concept of blood transmitted metastases and a recent study identifying prostatic cells in the blood of patients with metastatic prostate cancer.

More recently, Katz et al "Molecular Staging Of Prostate Cancer With The Use Of Enhanced Reverse Transcriptase-PCR Assay" *Urology* 43, p. 765-775 (1995), developed a reverse transcriptase-PCR assay using prostate specific antigen (PSA) primers to detect prostate cells in the circulation. They showed a significant correlation with capsular penetration and tumor positive surgical margins and suggest that their assay provides a specific means to stage apparent localized cancer prior to radical prostatectomy. The utility of reverse transcriptase-PCR assay has been confirmed by other investigators.

Although great strides have been made in the discovery of new prostatic tumor markers which have advanced our knowledge in the management of this disease, the ideal tumor marker is one produced in the course of the malignant process by the prostate only and elaborated into the peripheral circulation on metastasizing and eventually excreted in the urine. In recent years, studies on the steroid 5α-reductase enzyme in the human prostate have gained significance due to its role in the conversation of testosterone to dihydrotestosterone, the latter having been implicated in the development of benign and neoplastic growth. In 1992, evidence was presented for the existence of two steroid 5α-reductase isozymes in man. In humans, the type 2 predominate in the fetal genital skin, male accessory sex organs, and in the prostate. To date, there have not been any reports in the literature of the detection of either isozyme of 5α-reductase in the peripheral circulation or in the urine.

SUMMARY OF THE INVENTION

Basically, the present invention relates to a method for detecting prostatic cancer in patients and to biomarkers for use thereon. More particularly, the method comprises the detection of the presence of 5α-reductase type 2 isozyme is the serum or urine of patients.

In accordance with the invention, an immunological response is elicited to 5α-reductase type 2 isozyme found in the urine or serum of patients. Preferably, the urine or serum is treated with polyclonal antibodies to a peptide representing amino acids 28 to 43 of the 5α-reductase type 2 isozyme.

It is a general object of the invention to provide a method for detecting prostate cancer in patients by the detection of 5α-reductase type 2 isozyme in serum or urine.

It is a further object of the invention to provide a biomarker for detecting prostatic cancer.

Other objects and advantages of the invention will become apparent from the drawings and a reading of the preferred embodiments of the invention.

DESCRIPTION OF THE PREFERRED EMBODIMENTS

According to the present invention, a novel biomarker is utilized for detection of prostatic cancer. Polyclonal antibodies are prepared to a peptide representing amino acids 28 to 43 of the 5α-reductase type 2 isozyme. Using immunoaffinity-purified antibodies, the blood or urine of patients can be examined using Western blot following polyacrylamide gel electrophoresis. Positive bands can be detected in urine or sera of patients with prostatic cancer at 42 kDa compatible with the purified native glycosylated 5α-reductase type 2. These bands are nullified on the coincubation of the antibody of the biomarker peptide.

A typical Western blot of sera from 10 patients, shows that six patients developed a positive band at approximately 42 kDa whereas four patients were negative. The band at 42 kDa is compatible with the reported molecular weight of human 5α-reductase type 2 derived by SDS-PAGE analysis for the purified glycosylated enzyme. These bands were nullified on coincubation of the antibody with the tetramer peptide Cys-Ala-Lys followed by Pro (10 μ/ml). Twenty-one patients out of 28 with known adenocarcinoma of the prostate tested positive by Western blot. 13 of 22 patients with benign prostatic hypertrophy tested positive whereas 4 out of 12 patients with no history of prostatic disease tested positive.

To gain further insight as to the nature of the antigen which was producing a positive band at 42 kDa, the serum of a patient was concentrated fourfold and examined by two dimensional electrophoresis. To remove large protein aggregates, 0.5 ml of saturated ammonium sulfate was added slowly with agitation to 1.0 ml of serum and the mixture stored at 4° C. for 4 hours. The precipitated proteins were removed by centrifugation in the cold at 8000 G's for 10 minutes and the supernatant concentrated fourfold using a Microcon-3 microconcentrator (Amicon) at 16,000 G's. The concentrated serum was diluted with an equal volume of running buffer and 20 μl aliquots were applied to multiple lanes of an isoelectric focusing gel, pH 3-7. Parallel lanes of the developed gel were cut out and run in duplicate on SDS-PAGE gels. One gel was stained and the other blotted onto nitrocellulose for immunoblotting. A single band is prominent on the Western blot at approximately 42 kDA and pH 5 and a comparable band can be seen under the heavy protein band on the stained gel at the same location corresponding to the blot. In the Western blot, coincubation of the antibody with the tetramer peptide (hereinafter mentioned) obliterated the band at 42 kDa. The above results were confirmed when these experiments were repeated with serum 9 from a patient who had undergone bilateral orchiectomy following a diagnosis of adenocarcinoma of the prostate.

EXAMPLE 1

Antibody Preparation

A. Polyclonal antipeptide antibodies were prepared by Quality Controlled Biochemicals, Inc. (Hopkinton, Mass.) following standard protocols in New Zealand white rabbits. The peptide synthesized represented amino acids 28 to 43 of 5α-reductase type 2 with a cysteine residue on the N-terminal end and an amide group on the C-terminal end. The selection of this peptide followed a comparison of the amino acid sequences described by Normington and Russell for both the human and rat 5α-reductases 1 and 2. An analysis of these sequences showed that the N-terminal area of human 5α-reductase 2 encompassing amino acids 28 to 43 was suited to the production of a discriminating antibody to human 5α-reductase 2. The sequence of amino acids in the synthesized tetramer peptide was as follows:

with Novex Gel-Clear destain (LC 4625) to remove background color, minimum 2 hours at room temperature on a platform rocker or overnight at 4° C. To remove the acetic acid and shrink the gel slightly to facilitate handling, it was transferred into 20% ethanol and gently rocked for 10 minutes, drained and repeated a second time. The 20% alcohol was drained and the lane to be transferred (8×60 mm) was cut out by pushing a sharp straight blade through the gel. The strip was transferred to a V-shaped multichannel pipette basin containing 2 ml sample buffer (Novex LC 5371) and 0.5 ml ethanol and equilibrated for 3–5 minutes. The sample buffer was aspirated off, the gel strip rinsed once with running buffer (Novex LC 1675) and then transferred to a 1 mm×2D well 10–20% tricine precast gel (Novex EC 6626) designed to accommodate the gel strip. The gel was electrophoresed for 90 minutes at 125 volts constant and then blotted onto a nitrocellulose membrane as described previously.

The nitrocellulose membrane was rinsed in deionized water, incubated for 1 hour at 37° C. in blot buffer (5% carnation non-fat dry milk in PBS) and then washed in

SEQ ID NO:1

```
-----28  29   30   31   32   33   34   35   36   37   38   39   40   41   42   43-----
H2N—Cys—Ala—Lys—Pro—Ser—Gly—Tyr—Gly—Lys—His—Thr—Glu—Ser—Leu—Lys—Pro—Ala-amide
```

B. The antibodies to the peptide in the antisera collected following immunization were subjected to affinity purification on a sulfolink coupling gel (Pierce, Rockford, Ill.) according to procedures described in Antibodies, a Laboratory Manual, Cold Spring Harbor Laboratory. The immunoaffinity purified antibody was stored in lyophilized form at −80° C.

EXAMPLE 2

Immunoblotting

Utilizing the Novex Mini-Cell X Cell II (San Diego, Calif.) electrophoresis system, 5 μl of serum from a patient was diluted with an equal volume of sample buffer (Novex LC 1676) was applied to each lane of a 10 lane 10–20% tricine precast gel (Novex LC 6625). Separation was achieved in 90 minutes at 125 volts constant with Tricine SDS running buffer (Novex LC 1675). Gels were blotted onto nitrocellulose membranes using the Novex Blot Module in the same mini-cell. The composition of the transfer buffer 12 mM Tris, 96 mM glycine, pH 8.3, the transfer being completed at 30 volts constant in 90 minutes.

For two dimensional separations prior to immunoblotting, 5 μl of serum diluted with an equal volume of sample buffer (Novex LC 5371) was applied to one of ten wells of an isoelectric focusing gel (IEF), pH 3–7 (Novex EC 6655-B). Using the Novex cathode buffer (LC 5370) and anode buffer (LC 5300), optimal separation was achieved at 100 volts for 1 hour, 200 volts for 1 hour and 500 volts for 30 minutes. The gel was removed from the cassette and fixed for 30 minutes in a solution of 3.5% sulfosalicylic acid and 11.5% trichloroacetic acid. The gel was then rinsed in several changes of deionized water to remove fixing solution and stained for 5 minutes with 0.1% coomassie blue in 40% ethanol, 10% glacial acetic acid. The gel was then destained PBS-Tween (0.05% Tween 20 in PBS, pH 7.4) for 1 hour at room temperature with rocking. The membrane was transferred to a 25×150 mm Petri dish containing approximately 25 ml antibody (10 ug/ml PBS-Tween) to the peptide and incubated overnight at 4° C. The membrane was washed four times with PBS-Tween, the first time with rocking for 15 minutes. It was then transferred to a Petri dish containing 25 ml of a 1/30,000 dilution of an anti-rabbit immunoglobulin alkaline phosphatase conjugate affinity isolated antibody (Sigma A 3687) and incubated for 1 hour at room temperature. After washing in PBS-Tween as previously described, the membrane was transferred into a Petri dish containing 20 ml 5-bromo-chloro-4-indoyl phosphate/nitro blue tetrazolium substrate solution (Sigma BCIP/NBT, B-5655) and incubated at room temperature with rocking until a blue color developed.

EXAMPLE 3

Enzyme-Linked Immunosorbent Assay (ELISA) For 5α-Reductase In Serum Or Urine A stock solution of 1 μg/ml CAKP peptide standard in carbonate/bicarbonate buffer, pH 9.6 and working standard solutions of 1,5,10,15 and 20 ng/ml from stock was prepared. 100 μl of carbonate/bicarbonate buffer was added to the blank well of Example 2 and 100 μL of working standards either test sera or test urines at desired dilutions to the remaining wells of a 96 well Corning disposable sterile ELISA plate. The plate was covered and incubated for 2 hours at 37° C. and then overnight at 4° C. In one motion, the plate was inverted and the contents of the plate was placed into a waste receptacle and then rap plated against paper towels several times to remove excess solution. All wells were washed with phosphate buffered saline (PBS)/0.05% Tween 20 three times removing solution each time as previously described. 200 µl 1% BSA (bovine serum albumin) PBS was added to all wells, the plate was covered and incubated for 2 hrs. at 37° C. All wells with PBS/Tween 20 were washed as previously described and 100 µl of the antibody to the peptide diluted with PBS/Tween 20 to a concentration of 10 µg/ml was added. The plate was covered and incubated for 90 minutes at 37° C. All wells were washed with PBS/Tween 20 as previously described and 100 µl of anti-rabbi IgG alkaline phosphatase conjugate (Sigma A3687) diluted to 1/30,000 in PBS/Tween 20 was added. The plate was covered and incubated 90 minutes at 37° C. 100 µl of p-nitrophenyl phosphate substrate (Sigma Fast PNPP substrate tablet set, N-2770) was added and the mixture incubated 90 minutes at 37° C. The developed color at 405 nm in a microplate reader (Bio-Tek Instruments Kinetic Reader Model EL 312E) was read and the concentrations were calculated from a standard curve.

EXAMPLE 4

A. Immunoaffinity Purification of Antigen

Using Pierce Immunopure Protein A IgG Orientation Kit (44898), an antibody immunoaffinity column was prepared with 8.8 mg immunoaffinity purified antibody to the peptide. Sample preparation, column preparation and equilibration, binding of the antibody to the Protein A column, crosslinking of the bound antibody, blocking of remaining active sites and storage of the immobilized column was according to the Pierce protocol.

B. Gel Filtration Chromatography

Analysis of immunoaffinity purified antigen was performed by HPLC using a Perkin-Elmer system consisting of a LC-235 variable wavelength diode array detector, LCI-100 laboratory computing integrator, and a binary LC Pump Model 250 equipped with a 7125 Rheodyne injector with 100 µl fixed loop, a scavenger column, PE TSK SW guard column and a PE TSK G2000SW gel filtration analytical column (7.5 mm ID ×30 cm long). The mobile phase was 0.1M potassium phosphate buffer, pH 6.6, at a flow rate of 1.0 ml/min, detection at 220 nm.

C. Amino Acid Sequencing

Amino acid sequencing was accomplished by blotting 10–20% tricine gels onto PVDF membranes using the same conditions described for nitrocellulose membranes. Individual bands on the PVDF membrane were cut out and submitted for N-terminal Edman degradation and sequencing on an Applied Biosystem Model 470A or 473A at the ICBR Protein Chemistry Laboratory, University of Florida (Gainesville, Fla.).

EXAMPLE 5

Detection of 5 Alpha-Reductase By Dot Blot In The Urine Of Patients With Prostate Cancer Nitrocellulose transfer membrane, 0.22 was cut into 3" squares and circles with a diameter of one cm and with a minimum separation of one cm between circles are inscribed with a pencil. 7.5 µl test CAKP peptide (100 µl/ml) is applied to one circle as a positive control and 7.5 µl test urine to each of the remaining circles keeping each blot within a 5 mm diameter. The membrane was dried gently with a warm stream of air and transferred to a Lab-Tek square Petri dish (96 mm square by 16 mm deep) containing 10 ml blot buffer (5% carnation non-fat dry milk in PBS) and incubated 1 hr. at 37° C. The membrane is rinsed with PBS-Tween (0.05% Tween 20 in PBS, pH 7.4) several times and then incubated with 10 ml antibody (4 µg/ml in blot buffer) for 2 hours at room temperature with rocking. Following rinsing several times with PBS-Tween, the membrane was incubated sequentially with the same immunoglobulin alkaline phosphatase conjugate and substrate as described for the Western blot. The development of a blue dot indicated a positive finding.

EXAMPLE 6

Detection Of 5 Alpha-Reductase Type 2 By Western Blot In The Urine Of Patients With Prostate Cancer Utilizing the Novex Mini-Cell X Cell II (San Diego, Calif.) electrophoresis system, 7.5 pl of URINE, diluted with an equal volume of sample buffer (Novex LC 1676) was applied to each lane of a 10 lane 10–20% tricine precast gel (Novex LC 6625). The tetramer peptide was used as a positive control in one lane. Separation was achieved in 90 minutes at 125 volts constant with Tricine SDS running buffer (Novex LC 1675). Gels were blotted onto nitrocellulose membranes using the Novex Blot Module in the same mini-cell. The composition of the transfer buffer was 12 mM Tris, 96mM glycine, pH 8.3, the transfer being completed at 30 volts constant in 90 minutes.

The nitrocellulose membrane was rinsed in deionized water, incubated for 1 hour at 37° C. in 10 ml blot buffer (5% carnation non-fat dry milk in PBS) in a Lab-Tek square Petri dish (16×96 mm) and then washed in PBS-Tween (0.05% Tween 20 in PBS, pH 7.4) for 1 hour at room temperature with rocking. The membrane was transferred to a 16×96 mm Petri dish containing 10 ml antibody (4 µg/ml PBS-Tween) to the CAKP peptide and incubated overnight at 4° C. The membrane was washed four times with PBS-Tween, the first time with rocking for 15 minutes. It was then transferred to a Petri dish containing 10 ml of a 1/30,000 dilution of an antirabbit immunoglobulin alkaline phosphatase conjugate affinity isolated antibody (Sigma A 3687) and incubated for 1 hour at room temperature. After washing in PBS-Tween as previously described, the membrane was transferred into a Petri dish containing 10 ml 5-bromo-4-chloro-3-indoyl phosphate/nitro blue tetrazolium substrate solution (Sigma BCIP/NBT, B-5655) and incubated at room temperature for 30 minutes with rocking. A blue band develops at 97.5 kDa if the 5 Alpha-reductase immunoglobulin complex is present in the urine indicating a positive finding for prostate cancer.

EXAMPLE 7

A Screening Study Of Female and Male Urine To Establish Efficacy Of The Invention A total of 107 urines, 46 female and 61 male, were collected from patients. The females urines were collected to serve as negative controls whereas the male urines were collected from men with no history of prostatic disease and from men with a history of prostatic disease. All urines were sent to the laboratory coded so that laboratory personnel could not identify the urine with gender or disease state, if any. The urines were analyzed by Western blot and later by ELISA (enzyme-linked immunosorbent assay).

The summary of the Western blot analysis are shown in Table I. There were a total of 46 women in the female control group, 26 women in the premenopausal group and 20 in the postmenopausal group. Forty-five of the 46 women tested negative, the only female testing positive was a 33 year old woman with nephritis. There were a total of 45 men in the male control group which tested negative. These men had normal PSA's and no history of adenocarcinoma of the prostate. There were a total of 16 men in the male test group. Four men in this group with adenocarcinoma of the prostate, currently being treated with Lupron/Flutamide to contain the disease, tested negative. Two males with transitional cell carcinoma invading the prostatic ducts tested positive and two males with basal cell hyperplasia of the prostate with intraductal dysplasia also tested positive. Four males with elevated PSA's and no pathology report tested positive. The latter group will be followed clinically and monitored.

TABLE I

Western Blot Summary of 5α-Reductase Assay In Urine

| No. | Age Group | Negative | Positive | Comments |
|---|---|---|---|---|
| A. | Female Control Group | | | |
| 25 | 29–50 | 50 | 0 | Premenopausal |
| 20 | 51–81 | 20 | 0 | Postmenopausal |
| 1 | 33 | 0 | 1 | Neophritis |
| — | | — | — | |
| 46 | | 45 | 1 | |

TABLE I-continued

Western Blot Summary of 5α-Reductase Assay In Urine

| No. | Age Group | Negative | Positive | Comments |
|---|---|---|---|---|
| B. | Male Control Group | | | |
| 3 | 6–12 | 3 | 0 | None |
| 38 | 46–83 | 38 | 0 | Normal PSA |
| 4 | 53–63 | 4 | 0 | BPH[1] |
| — | | — | — | |
| 45 | | 45 | 0 | |
| C. | Male Test Group | | | |
| 4 | 68–80 | 4 | 0 | Footnote[2] |
| 4 | 63–83 | 0 | 4 | Footnote[3] |
| 2 | 72–75 | 0 | 2 | Footnote[4] |
| 2 | 83–85 | 0 | 2 | Footnote[5] |
| 4 | 66–78 | 0 | 4 | Footnote[6] |
| — | | — | — | |
| 16 | | 4 | 12 | |

[1] Benign prostatic hypertrophy
[2] Under treatment with Lupron/Flutamide for adenocarcinoma of the prostate
[3] Adenocarcinoma of the prostate, elevated PSA, untreated
[4] Transitional cell carcinoma invading prostatic ducts
[5] Basal cell hyperplasia with intraductal dysplasia
[6] Significantly elevated PSA's but not pathology report available

What is claimed is:

1. A method for detecting prostatic cancer in patients which comprises the step of detecting the presence of 5α-reductase type 2 enzyme in the serum or urine of said patients with an antibody specific for the peptide consisting of SEQ ID NO: 1.

2. The method of claim 1, wherein said 5α-reductase type 2 enzyme is detected by Western blot of sera.

3. The method of claim 1, wherein said 5α-reductase type 2 enzyme is detected in urine by Western blot or ELISA.

* * * * *